(12) United States Patent
Durst et al.

(10) Patent No.: US 7,317,784 B2
(45) Date of Patent: Jan. 8, 2008

(54) MULTIPLE WAVELENGTH X-RAY SOURCE

(75) Inventors: Roger D. Durst, Middleton, WI (US);
Bob Baoping He, Madison, WI (US);
Carsten Michaelsen, Geesthacht (DE);
Chuji Katayama, Inazawa (JP)

(73) Assignee: Broker AXS, Inc., Madison, WI (US)

( * ) Notice: Subject to any disclaimer, the term of this patent is extended or adjusted under 35 U.S.C. 154(b) by 0 days.

(21) Appl. No.: 11/335,161

(22) Filed: Jan. 19, 2006

(65) Prior Publication Data
US 2007/0165780 A1    Jul. 19, 2007

(51) Int. Cl.
*H01J 35/08*   (2006.01)
(52) U.S. Cl. .......................... 378/124; 378/84
(58) Field of Classification Search ................ 378/119, 378/124, 136, 137, 138, 84, 85
See application file for complete search history.

(56) References Cited

U.S. PATENT DOCUMENTS

| | | | |
|---|---|---|---|
| 3,525,863 A * | 8/1970 | Constantine et al. ......... 378/45 |
| 5,357,552 A * | 10/1994 | Kutschera ................... 378/132 |
| 6,195,410 B1 * | 2/2001 | Cash, Jr. ...................... 378/43 |
| 7,072,442 B1 * | 7/2006 | Janik ........................... 378/84 |
| 2003/0156682 A1 * | 8/2003 | Yokhin et al. ................ 378/70 |
| 2006/0115047 A1 * | 6/2006 | Yokhin ........................ 378/70 |

* cited by examiner

*Primary Examiner*—Hoon Song
(74) *Attorney, Agent, or Firm*—The Law Offices of Paul E. Kudirka

(57) ABSTRACT

A multiple wavelength X-ray source includes an electron-generating cathode and an anode with multiple target regions, each of which emits X-rays at a different characteristic wavelength in response to the electrons. The different X-ray radiation outputs are focused by different focusing sections of a focusing optic. The multiple focusing sections are in different respective locations, and each focuses its respective X-ray radiation onto a sample. The focusing sections may be side-by-side mirrors in a Kirkpatrick-Baez configuration, or in a single-bounce, doubly curved elliptical configuration.

25 Claims, 2 Drawing Sheets

MULTIPLE WAVELENGTH X-RAY SOURCE

FIELD OF THE INVENTION

This invention relates generally to X-ray diffraction analysis and, more particularly, to X-ray sources used in X-ray diffraction analysis.

BACKGROUND OF THE INVENTION

X-ray diffraction analysis uses X-ray energy focused on a target material of interest to determine structural qualities of the material. For a particular material, and X-rays at a particular wavelength, the X-ray energy is diffracted and forms a diffraction pattern that may be detected with a detector to yield information regarding the material structure. Conventional X-ray sources are able to generate only a single wavelength as they rely on characteristic Kα radiation from a particular target material. That is, these sources function by illuminating a material target with a high energy electron beam. This excites both continuum Bremsstrahlung radiation and also characteristic line emission. For most analytical applications, a monochromator is used to isolate only the characteristic line emission.

Particular X-ray energies may be generally preferable for certain applications. For example, for small molecules, highly absorbing samples, charge density measurements or for work with diamond anvil cells, relatively short wavelength Mo radiation ($\lambda=0.73$ Å) is most often employed. For protein crystallography or determining the absolute structure of light-atom organic molecules, a longer wavelength is preferred (in most cases, copper with $\lambda=1.54$ Å). In some other specialized experiments, silver, chromium or cobalt might be preferred.

If one wishes to change the operating wavelength of an X-ray source, the target material of the source may be changed. However, this changeover procedure can be tedious and time-consuming. This is especially true for high-brilliance rotating anode generators. In order to change the target in a conventional rotating anode, the system must first be powered down (and the rotating of the anode stopped), the vacuum chamber must be opened, the anode must be disconnected, dismounted and replaced, the vacuum must then be reestablished, and the new anode must be restarted and reconditioned. After the target has been changed, the X-ray optics must also be replaced if one is using modern multilayer optics, which operate optimally only at a single fixed wavelength. Also, since the optics will have different take off angles, the goniostat will typically have to be repositioned and the optics thereafter realigned. This entire process can easily take from several hours to an entire day to complete.

In order to address this difficulty, sources have been proposed that may operate at two different wavelengths. U.S. Pat. No. 4,007,375 discloses a multiple wavelength X-ray tube in which one of several target materials may be selected by electrostatic deflection of an incident electron beam. A similar design shown in Japanese patent JP5135722 has a multiple wavelength X-ray source in which the tube consists of several tracks composed of different materials deposited on a rotating anode. One of the target materials is selected by deflecting the incident electron beam magnetically. In both of these patents, however, the associated monochromator optics would have to be changed and aligned, so there is no means by which a system could change immediately from operation at one wavelength to operation at another.

Japanese patent JP2848944 discloses a dual wavelength X-ray source which also uses an anode with two tracks composed of different respective target materials. In this case, however, the cathode filament is physically moved to change the wavelength. But the optics must also be changed and aligned, so that operation at the new wavelength is not instantaneous. This is also the case in Japanese patent JP11339703, which has multiple target materials and an electron gun that is rotated to select the wavelength.

U.S. Pat. No. 6,041,099 describes a side-by-side Kirkpatrick-Baez multilayer optic that is a multilayer monochromator and beam conditioning optic for the focusing of an X-ray beam onto a sample. This optic is comprised of two multilayer mirrors attached to each other at a relative angle of 90°, and it has a single corner in which two-dimensional beam collimation or focusing takes place. This arrangement, often referred to as a "Montel optic" according to its first mention, also appears in U.S. Pat. No. 6,014,423, in which a combination of such optics is described which has multiple corners, typically four, to reflect the X-rays, with the aim of enhancing the X-ray flux. The configuration allows for the reflection of radiation from a single anode to a sample position.

U.S. Pat. No. 6,421,417 describes a multilayer optic with adjustable working wavelength. Here, for a wavelength change, the optic either needs a change of the curvature, or the multilayer structure is configured to include a plurality of d-spacings, or the optic is formed with stripe-like multilayer coating sections. A change of the curvature requires a major realignment of the optic. The use of a plurality of d-spacings leads to a compromise where the performance is lower than the performance of two optics that are fully optimized for their individual working wavelengths, in addition to requiring a major realignment of the optic. Stripe-like multilayer coatings cannot be used with a Montel arrangement, and in a stripe-like multilayer, the optic has a single, fixed curvature. Therefore, the optics cannot be fully optimized for best performance at the different wavelengths.

U.S. Pat. No. 6,917,667 discloses a multilayer optic that can be used for two wavelengths, but for which the wavelength change requires a realignment of the optic. Further, the principle described in this patent functions only if the two wavelengths are close to each other, e.g., for Cu and Co radiation, because it neglects the effect of refraction, which is wavelength-dependent. Therefore, the principle of this patent functions only when the two wavelengths are appropriately selected. Since the optic of this patent is a compromise, the performance at the two wavelengths is reduced compared to optics that are fully optimized for a single working wavelength. Furthermore, the length of these optics is limited to typically 40 mm, leading to a rather small opening aperture and small capturing efficiency.

SUMMARY OF THE INVENTION

In accordance with the present invention, a multiple wavelength X-ray source is provided for directing X-ray energy to a sample. The source includes a cathode that emits electrons and an anode upon which the electrons are incident. The anode uses a plurality of different target materials, each of which generates X-ray radiation at a different characteristic wavelength in response to the incident electrons. The different materials are at different locations relative to the sample so that the emitted radiation for each material has a different starting location. In order to provide the proper focusing for the X-ray energy output from each respective target material, a focusing optic is provided that has a plurality of focusing sections, each with a different relative fixed location. Each focusing section focuses the X-ray radiation corresponding to a different one of the characteristic wavelengths onto the sample. This removes the need for changing or repositioning the optic when changing wavelengths, and allows a user to make an effectively "instantaneous" wavelength change.

The optic used with the present invention may comprise two side-by-side mirrors, each focusing a different one of two different characteristic wavelengths. The mirrors may each have, for example, a Kirkpatrick-Baez configuration, or a single-bounce, doubly curved elliptical configuration. The mirrors may be fixed in position relative to each other, and may each be a different distance from the sample. In addition, it is possible that the two mirrors may have a different respective overall length in a first direction, e.g., along a path between the anode and the sample.

The cathode used with the present invention may be arranged so as to provide electrons selectively to the different target materials of the anode. One possible arrangement might be a dual-segment filament, with each filament segment being individually energizable. The energizing of a given filament segment results in the directing of electrons to a different one of the target materials of the anode. The anode itself may be a rotating anode, and the target materials of the anode may rotate together. Although the different focusing sections of the focusing optic are in different locations, they are independent, and may focus the X-ray radiation emitted from a particular target material to a desired location. Thus, each focusing section may be arranged to focus its respective X-ray radiation onto the same region of the sample, or they may be arranged to focus the different X-ray wavelengths onto different regions of the sample.

BRIEF DESCRIPTION OF THE DRAWINGS

The above and further advantages of the invention may be better understood by referring to the following description in conjunction with the accompanying drawings in which.

DETAILED DESCRIPTION

Figure 1:
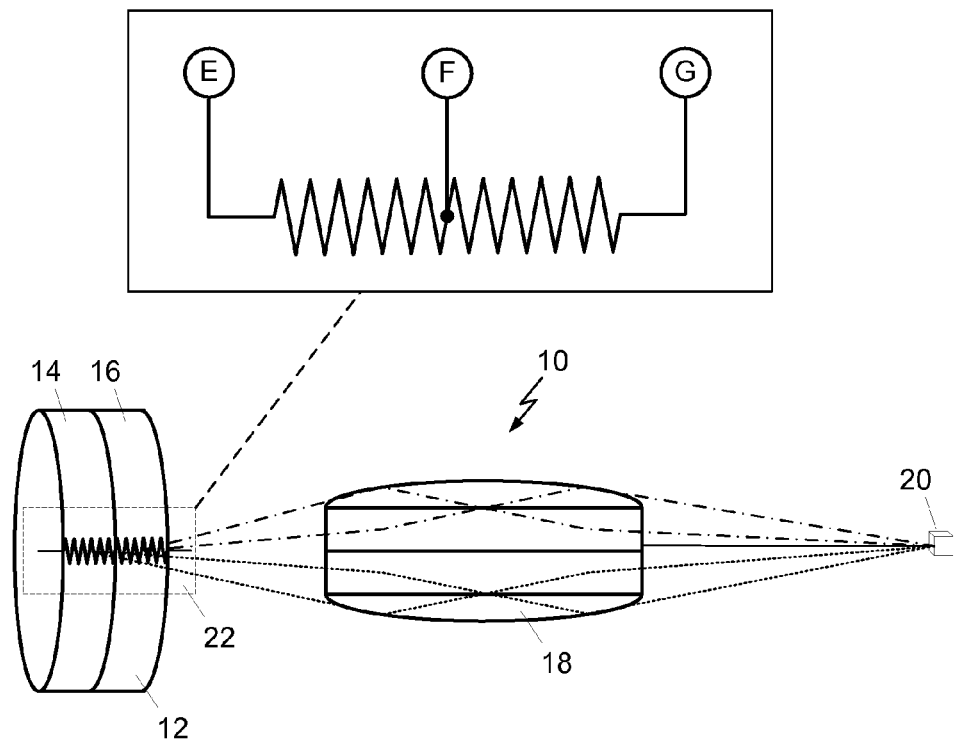
FIG. 1 is a schematic top view of a multiple wavelength X-ray source according to the present invention.

Shown in FIG. 1 is a schematic depiction of a multiple wavelength X-ray source 10 according to the present invention. The source uses a rotating anode 12 that has a target with two different materials. For example, a first section 14 could be made of copper, while a second section 16 could be made of molybdenum. Many other possible material combinations are also possible. The two target materials are chosen such that each provides a different characteristic X-ray wavelength when excited. Both rotate together, and are located relative to focusing optic 18 so that X-ray radiation from the anode may be received by the optic, and focused onto a sample 20 under investigation.

To provide selective wavelength generation, a two segment cathode 22 is located adjacent to the anode. In FIG. 1, an inset is provided that shows a larger view of the cathode. Three electrical terminals are connected to the cathode are shown and are labeled, respectively, "E", "F" and "G". By applying an electrical potential across selected ones of the terminals, different portions of the cathode may be energized. The cathode is aligned with the rotating anode so that energizing of the different cathode portions results in excitation of different sections of the anode and, correspondingly, the generation of X-ray energy at different wavelengths. For example, with the cathode positioned as shown in FIG. 1, placing an electrical potential across terminals "E" and "F" (the "first portion" of the cathode) causes electron bombardment of first section 14 of the anode which, if the first section is copper, results in the generation of X-rays at a wavelength of $\lambda=1.54$ Å. Similarly, if an electrical potential is placed across terminals "F" and "G" of the cathode, the "second portion" of the cathode is energized, causing electron bombardment of the second anode section 16. If the second anode section is, for example, molybdenum, this would result in the generation of X-rays at a wavelength of $\lambda=0.73$ Å.

Whichever section of the anode is excited, it is desirable to focus the X-rays onto the target 20. Due to the different respective locations of the first and second sections of the anode 12, there are slightly different optical parameters necessary to focus the X-ray outputs of section 14 and section 16 of the anode, respectively. Therefore, the present invention uses a dual-wavelength mirror assembly as focusing optic 18. The mirror assembly shown in FIG. 1 is divided into two sides. Each side is a "Kirkpatrick-Baez" optic or, alternatively, a pair of single-bounce doubly curved elliptical optics. The two sides of the optic have focal lengths and take off angles optimized so that the two separate characteristic wavelengths that can be emitted by the dual-material target anode are both focused onto the sample. In this example, the two sides of the mirror are prealigned and joined together to simplify the alignment by reducing the number of degrees of freedom.

The mirror assembly 18 differs from those of the prior art that have a plurality of side-by-side multilayer mirrors joined together to provide reflectors with four or more corners (such as U.S. Pat. No. 6,014,423). That prior art configuration does not use two or more mirrors having different focal lengths and take off angles such that they can direct the radiation from two separate anode segments onto precisely the same sample position. The ability to do this allows the present invention to change the wavelength of the source without realigning the optics. In addition, the prior art uses two optics that are joined together in a square or cylindrical configuration. This is not required with the present invention. Therefore, the mirror assembly 18 may be designed with any of a number of different separations between the two mirrors so as to optimize the takeoff angles for the different wavelengths.

Figure 2:
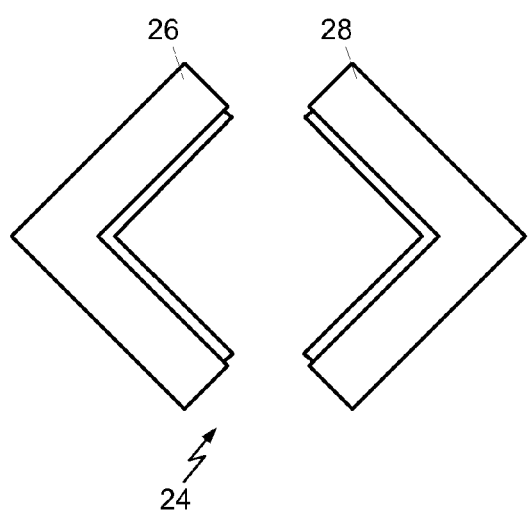
FIG. 2 is a schematic view of a focusing optic that may be used with the X-ray source of FIG. 1, wherein the optic comprises two side-by-side Kirkpatrick-Baez mirrors.

A schematic front view of a mirror assembly like that of FIG. 1 is shown in FIG. 2. Mirror assembly 24 includes first mirror 26 and second mirror 28. In this example, the mirrors are two side-by-side Kirkpatrick-Baez mirrors. It is not necessary that the first and second mirrors be the same distance from the anode. This is particularly true in the case for which the two focal spots on the X-ray target are located at different positions. In such a case, it may be advantageous to place each of the two mirrors at the same distance from its respective focal spot. In this arrangement, the same optical elements can be used as might be designed for a single wavelength configuration, and an expensive redesign of the optical elements would not be necessary. Moreover, the optical elements could have different respective lengths, which may be advantageous since shorter wavelengths may require longer optics in order to produce the same flux and divergence.

Figure 3:
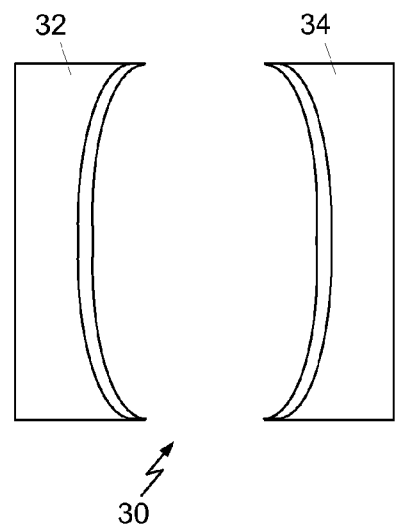
FIG. 3 is a schematic view of a focusing optic that may be used with the X-ray source of FIG. 1, wherein the optic comprises two single-bounce, doubly curved elliptical mirrors.

Another embodiment of the mirror assembly 18 is shown in FIG. 3. In the mirror assembly 30 shown in this figure, a first mirror 32 and a second mirror 34 are arranged face to face, just as the mirrors in FIG. 2. However, while the mirrors of FIG. 2 are based on a Kirkpatrick-Baez type arrangement, the mirrors in the FIG. 3 embodiment are single bounce elliptical mirrors. The mirrors 32, 34 are each optimized for one of the two wavelengths emitted by the dual wavelength anode, and are prealigned to a common focus position and then fixed together. The single-bounce elliptical mirrors of the FIG. 3 embodiment are like those described in the prior art, but are arranged relative to each other so as to provide the desired focusing of each of the two wavelengths without having to realign the optics.

Figure 4:
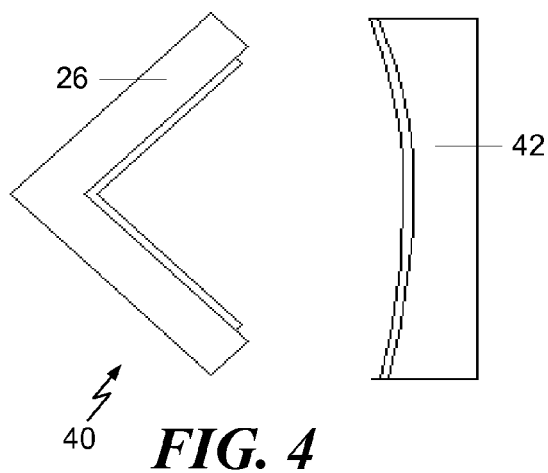
FIG. 4 is a schematic view of a focusing optic that may be used with the X-ray source of FIG. 1, wherein the optic comprises two side-by-side mirrors, each of which has a different configuration.

Another embodiment of the mirror assembly 18 is shown in FIG. 4. In the mirror assembly 40 shown in this figure, a first mirror 42 and a second mirror 44 are arranged face to face, also as the mirrors in FIG. 2. However, while the mirrors of FIG. 2 are both based on a Kirkpatrick-Baez type arrangement, mirror 42 in the FIG. 4 embodiment has a Kirkpatrick-Baez type arrangement whereas mirror 44 is a single bounce elliptical mirror.

Figure 5:
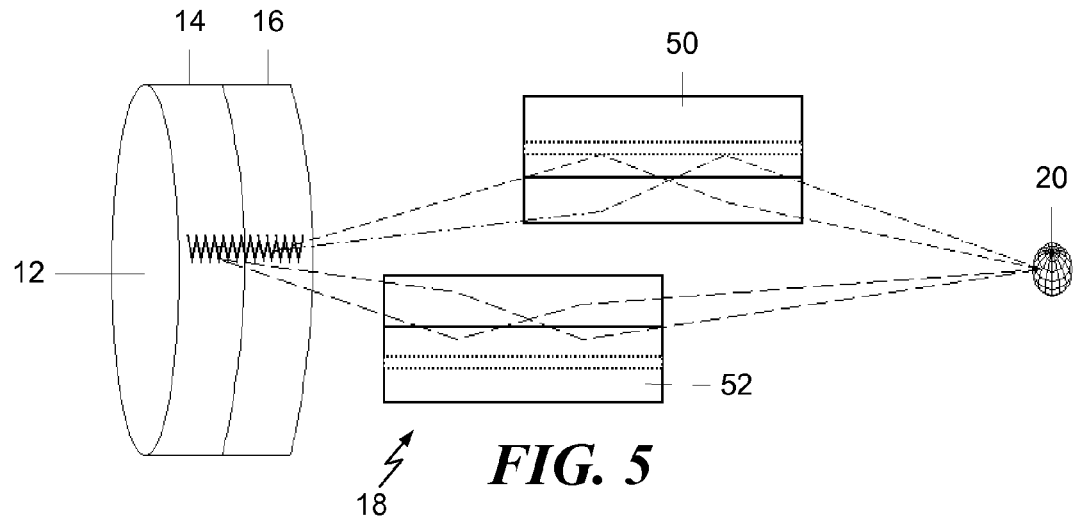
FIG. 5 is a schematic view of a focusing optic that may be used with the X-ray source of FIG. 1, wherein the optic comprises two side-by-side mirrors, each of which has a different distance from the sample.

FIG. 5 shows still another embodiment of the arrangement shown in FIG. 1 where the focusing optic 18 comprises two side-by-side mirrors, 50 and 52, each of which has a different distance from the sample 20.

Figure 6:
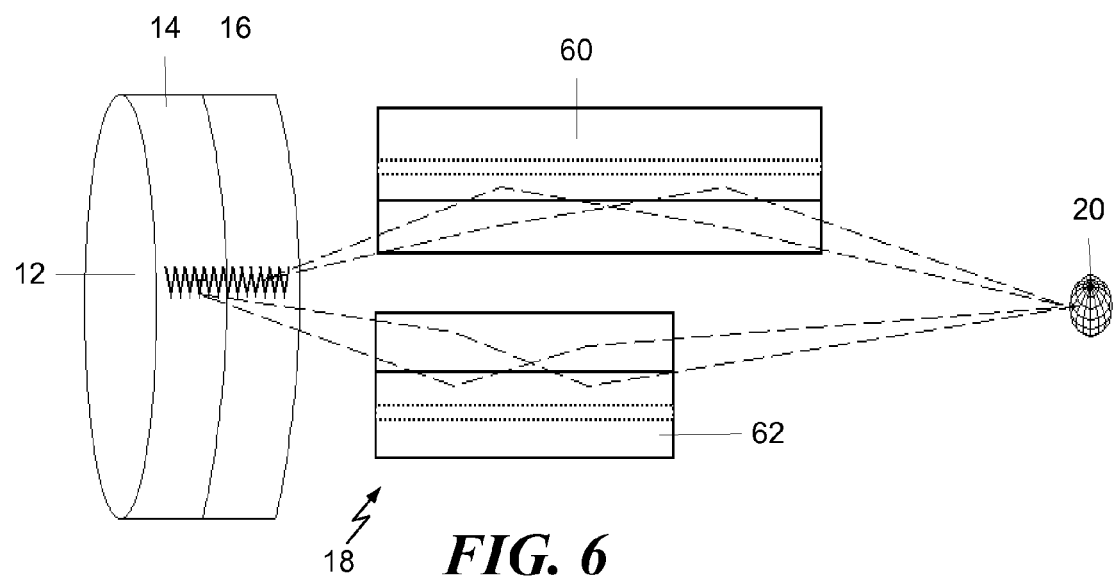
FIG. 6 is a schematic view of a focusing optic that may be used with the X-ray source of FIG. 1, wherein the optic comprises two side-by-side mirrors, each of which has a different respective overall length.

FIG. 6 shows yet another embodiment of the arrangement shown in FIG. 1 where the focusing optic 18 comprises two side-by-side mirrors, 60 and 62, each of which has a different respective length.

Those skilled in the art will recognize that with the dual wavelength source and the mirror assembly of the present invention, a user can switch between one wavelength and another simply by changing which section of the anode is activated, such as by energizing a particular portion of a cathode like that shown in FIG. 1. This change is a simple matter of electrical circuit design, and can be accomplished via a simple pushbutton control, or any other manual or automatic control available. The present invention also provides the means to emit both wavelengths simultaneously by energizing both sections of the cathode at the same time. In such a case, both wavelengths would be properly focused by their respective mirrors so that a user could focus both wavelengths on the target simultaneously. Those skilled in the art will also recognize that operation of the invention does not necessarily require the use of a segmented filament cathode with a dual target anode like that shown in FIG. 1. Two separate cathode filaments could be used instead. In fact, any other type of dual target anode could be, such as one with an electrostatically or magnetically deflected electron beam, could be used, as could a source with a movable or rotatable cathode. In each of these cases, the prealignment of the two mirrors of the mirror assembly will be such as to focus each of the wavelengths onto the desired region of the target.

While the invention has been shown and described with reference to a preferred embodiment thereof, it will be recognized by those skilled in the art that various changes in form and detail may be made herein without departing from the spirit and scope of the invention as defined by the appended claims.

What is claimed is:

1. A multiple wavelength X-ray source for directing X-ray energy to a sample, the source comprising:
   a cathode that emits electrons;
   an anode upon which the electrons are incident, the anode comprising a plurality of sections, each section consisting of a target material which generates X-ray radiation at a characteristic wavelength in response to the incident electrons, the sections consisting of different target materials that generate X-ray radiation at different characteristic wavelengths and each of the plurality of anode sections being located at a different position relative to the sample; and
   a focusing optic having a plurality of focusing sections each with a different relative fixed location, each focusing section focusing the X-ray radiation corresponding to a different one of the characteristic wavelengths onto the sample.

2. An X-ray source according to claim 1 wherein the optic comprises two side-by-side mirrors.

3. An X-ray source according to claim 2 wherein the mirrors each have a Kirkpatrick-Baez configuration.

4. An X-ray source according to claim 2 wherein the mirrors each have a single-bounce, doubly curved elliptical configuration.

5. An X-ray source according to claim 2 wherein the mirrors each have a different configuration.

6. An X-ray source according to claim 2 wherein the two mirrors are fixed in position relative to each other.

7. An X-ray source according to claim 2 wherein the two mirrors are each a different distance from the sample.

8. An X-ray source according to claim 2 wherein the two mirrors each have a different respective overall length in a first direction.

9. An X-ray source according to claim 1 wherein the cathode comprises a dual-segment filament, wherein each filament segment is individually energizable, and wherein the energizing of each filament segment results in the directing of electrons to a different one of the target materials of the anode.

10. An X-ray source according to claim 1 wherein the anode is a rotating anode.

11. An X-ray source according to claim 1 wherein each of the focusing sections focuses its respective X-ray radiation onto the same region of the sample.

12. An X-ray source according to claim 1 wherein each of the focusing sections focuses its respective X-ray radiation onto a different region of the sample.

13. A dual wavelength X-ray source for directing X-ray energy to a sample, the source comprising:
   a cathode that emits electrons along one of a first trajectory and a second trajectory in response to a user input;
   an anode upon which the electrons are incident, the anode comprising a first target material that generates X-ray radiation at a first characteristic wavelength in response to electrons following the first trajectory and a second target material different from the first target material that generates X-ray radiation at a second characteristic wavelength in response to electrons following the second trajectory; and a focusing optic having a first focusing section in a first location, and a second focusing section in a second location different from the first location, the first focusing section focusing the X-ray radiation corresponding to the first characteristic wavelength onto the sample and the second focusing section focusing the X-ray radiation corresponding to the second characteristic wavelength onto the sample, the first and second focusing sections being fixed in location relative to each other.

14. A method of directing X-ray energy to a sample, the method comprising:

generating electrons with a cathode;

receiving the electrons with an anode comprising a plurality of sections, each section consisting of a target material which generates X-ray radiation at a characteristic wavelength in response to the incident electrons, the sections consisting of different target materials that generate X-ray radiation at different characteristic wavelengths and each of the plurality of the anode sections being at a different position relative to the sample; and focusing the X-ray radiation with a focusing optic having a plurality of focusing sections each with a different relative fixed location, each focusing section focusing the X-ray radiation corresponding to a different one of the characteristic wavelengths onto the sample.

15. A method according to claim 14 wherein the optic comprises two side-by-side mirrors.

16. A method according to claim 15 wherein the mirrors each have a Kirkpatrick-Baez configuration.

17. A method according to claim 15 wherein the mirrors are each have a single-bounce, doubly curved elliptical configuration.

18. A method according to claim 15 wherein the mirrors each have a different configuration.

19. A method according to claim 15 wherein the two mirrors are fixed in position relative to each other.

20. A method according to claim 15 wherein the two mirrors are each a different distance from the sample.

21. A method according to claim 15 wherein the two mirrors each have a different respective overall length in a first direction.

22. A method according to claim 14 wherein the cathode comprises a dual-segment filament, wherein each filament segment is individually energizable, and wherein the energizing of each filament segment results in the directing of electrons to a different one of the target materials of the anode.

23. A method according to claim 14 wherein the anode is a rotating anode.

24. A method according to claim 14 wherein each of the focusing sections focuses its respective X-ray radiation onto the same region of the sample.

25. A method according to claim 14 wherein each of the focusing sections focuses its respective X-ray radiation onto a different region of the sample.

* * * * *

UNITED STATES PATENT AND TRADEMARK OFFICE
CERTIFICATE OF CORRECTION

| | |
|---|---|
| PATENT NO. | : 7,317,784 B2 |
| APPLICATION NO. | : 11/335161 |
| DATED | : January 8, 2008 |
| INVENTOR(S) | : Roger D. Durst et al. |

It is certified that error appears in the above-identified patent and that said Letters Patent is hereby corrected as shown below:

On the Title Page, Item 73,

Please replace "Broker AXS, Inc." with --Bruker AXS, Inc.--.

Signed and Sealed this

Thirtieth Day of December, 2008

JON W. DUDAS
*Director of the United States Patent and Trademark Office*